(12) United States Patent
Reynolds

(10) Patent No.: US 6,168,576 B1
(45) Date of Patent: Jan. 2, 2001

(54) DEVICE FOR DISPENSING VAGINAL MEDICATION

(76) Inventor: Irene N. Reynolds, 1804 Mountain Rd., Glen Allen, VA (US) 23060

( * ) Notice: Under 35 U.S.C. 154(b), the term of this patent shall be extended for 0 days.

(21) Appl. No.: 09/317,735

(22) Filed: May 24, 1999

(51) Int. Cl.[7] .......................... A61F 13/20; A61M 31/00; A61C 5/04; B43K 5/12
(52) U.S. Cl. ................. 604/15; 604/18; 604/60; 604/218; 604/288; 604/311; 401/170; 401/176; 401/192; 433/90
(58) Field of Search ...................... 604/11–18, 285–288, 604/57–60, 218, 311; 401/127, 170, 176, 192; 433/89, 90

(56) References Cited

U.S. PATENT DOCUMENTS

| | | | |
|---|---|---|---|
| 3,667,465 | * 6/1972 | Voss | 604/285 |
| 3,941,129 | * 3/1976 | Pleznac | 222/309 |
| 4,432,758 | * 2/1984 | Finegold | 604/288 |
| 4,466,426 | * 8/1984 | Blackman | 604/232 |
| 4,658,993 | * 4/1987 | Vlasich | 433/89 |
| 5,122,057 | * 6/1992 | Discko, Jr. | 433/90 |
| 5,397,312 | * 3/1995 | Rademaker et al. | 604/218 |
| 5,554,128 | * 9/1996 | Hedges | 604/192 |

* cited by examiner

Primary Examiner—Dennis Ruhl
(74) Attorney, Agent, or Firm—Norman B. Rainer

(57) ABSTRACT

A hand-operated disposable device for controllably dispensing medications having a paste-like or cream-like consistency includes a transparent plastic container member having a cylindrical medication-holding bore, and a plunger member which slidably engages the bore. The bore has a series of annular grooves corresponding to incremental volumes of the bore, and the plunger has a lip which interacts with the grooves.

5 Claims, 1 Drawing Sheet

DEVICE FOR DISPENSING VAGINAL MEDICATION

BACKGROUND OF THE INVENTION

1. Field of the Invention

This invention relates in general to a medication applicator, and more particularly concerns apparatus for the personally adjustable, accurate and sanitary application of vaginal medication.

2. Description of the Prior Art

Known devices for the intravaginal application of medication typically consist of a hollow tubular applicator having an internal piston. The medication, generally of cream-like consistency, is disposed within the hollow applicator and is extruded therefrom by means of the internal piston in the manner of a large, crude hypodermic syringe.

Typical devices for the application of vaginal medication are disclosed for example in U.S. Pat. Nos. 4,496,341; 4,557,720; 5,330,427; 5,397,312; and 5,788,664. Such devices are generally lacking in the control and adjustability of the depth of insertion and amount of medication dispensed.

In order to assure sanitary use and low risk of reinfection, disposable devices have been available which are discarded following a single use. However, such disposable units are generally sold with the medication already contained therein, and are intended to dispense their entire content of medication as a single dose. Such devices are generally not adaptable to variation in the medication type or dosage to accommodate the specific needs of particular individuals.

It is accordingly an object of the present invention to provide a disposable dispenser for the controlled application of vaginal medications.

It is another object of this invention to provide a dispenser as in the foregoing object which facilitates visual and tactile monitoring of medication being dispensed.

It is a further object of the present invention to provide a dispenser of the aforesaid nature permitting comfortable and adjustable insertion.

It is yet another object of this invention to provide a dispenser of the aforesaid nature of simple construction amenable to low cost manufacture.

These objects and other objects and advantages of the invention will be apparent from the following description.

SUMMARY OF THE INVENTION

The above and other beneficial objects and advantages are accomplished in accordance with the present invention by a device for controllably dispensing substances having a paste-like or cream-like consistency comprising:

a) a transparent plastic container member having a cylindrical bore elongated upon a straight axis between open leading and trailing extremities and having demarcation means disposed at spaced intervals along said axis to denote successive regions within said bore of known volume, and b) a plunger member elongated between forward and rearward extremities and removably associated with said container member by way of slidable engagement with said bore upon a common axis, said forward extremity having a transverse force-applying surface and surrounding outwardly protruding wiping lip, and said rearward extremity having abutment means interactive with the trailing extremity of said bore.

BRIEF DESCRIPTION OF THE DRAWING

For a fuller understanding of the nature and objects of the invention, reference should be had to the following detailed description taken in connection with the accompanying drawing forming a part of this specification and in which similar numerals of reference indicate corresponding parts in all the figures of the drawing.

DESCRIPTION OF THE PREFERRED EMBODIMENT

Figure 1:
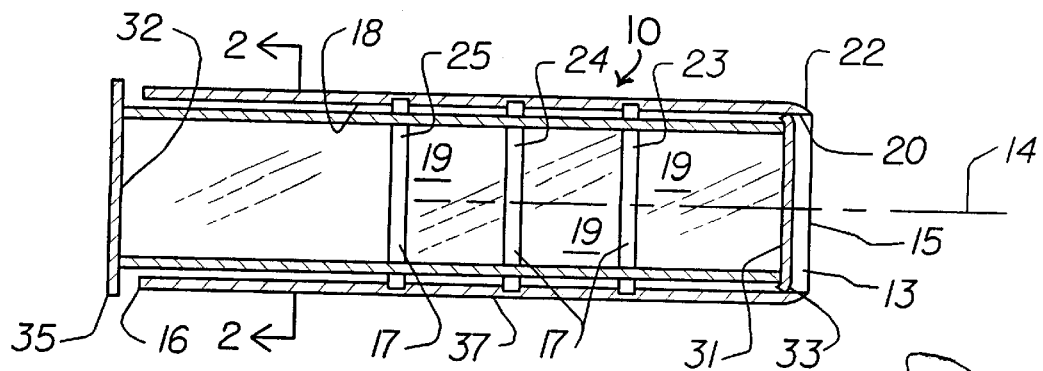
FIG. 1 is a sectional side view of an embodiment of the dispensing device of the present invention.
Figure 2:
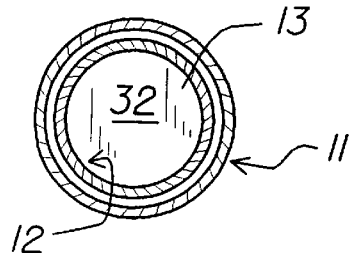
FIG. 2 is a sectional view taken in the direction of the arrows upon the line 2—2 of FIG. 1.
Figure 3:
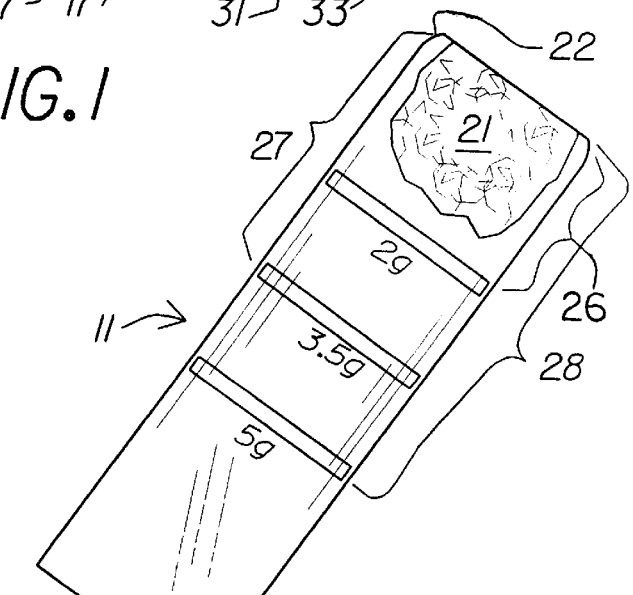
FIG. 3 is an exploded perspective view of the embodiment of FIG. 1, with a portion broken away to reveal interior details.
Figure 3:
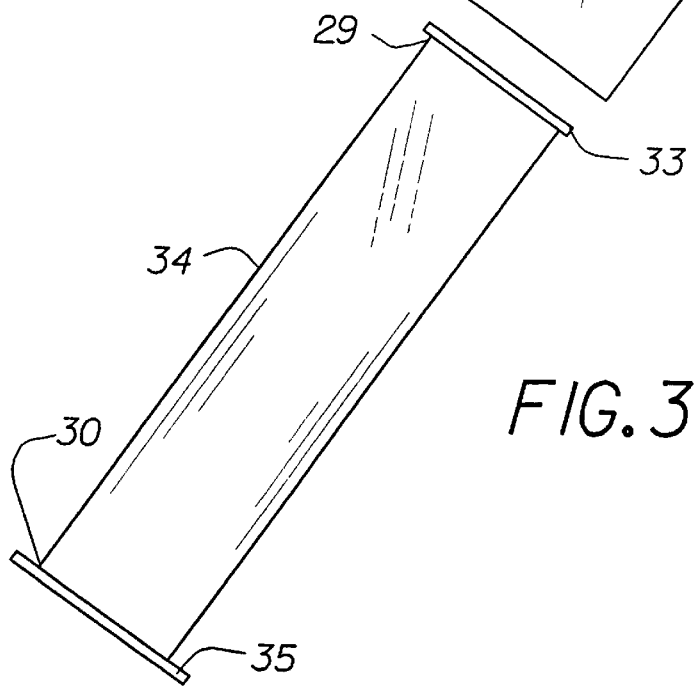

Referring now to FIGS. 1–3, an embodiment of the dispensing device 10 of the present invention is shown comprised of container member 11 and plunger member 12.

Said container member is fabricated of plastic material as a monolithic structure having a cylindrical bore 13 defined by sidewall 20 and elongated upon straight axis 14 between open leading and trailing extremities 15 and 16, respectively. Said cylindrical bore is preferably of circular cylindrical configuration, having an inside diameter of about 1.50 inch and a length between 6 and 7 inches. Leading extremity 15 is defined by a circular edge 22, which is rounded for comfort. Demarcation means in the form of a series of annular grooves 17 are fashioned within the smooth interior surface 18 of bore 13 at spaced intervals along axis 14. Said grooves denote successive regions 19 of known volume within said bore. A first groove 23 of said series is preferably located 1.25 inches from leading extremity 15. A second groove 24 of said series is preferably located 2.5 inches from said leading extremity, and a third groove 25 is located 3.25 inches from said leading extremity. The spacing of said grooves, in conjunction with the inside diameter of the bore creates incrementally cumulative regions 26, 27 and 28 which respectively hold approximately 2, 3.5 and 5 grams of cream type medications. Indicia may be located on exterior surface 37 of said container member adjacent said demarcation means to show the corresponding volume of the bore or approximate weight of medication.

The thickness of sidewall 20, and the nature of the plastic employed to fabricate said container member are chosen so as to cause said sidewall to be transparent. The term "transparent", as employed herein is intended to define a sidewall structure which permits the external visual discernment of opaque paste-like medication 21 disposed within said bore. Suitable plastics useful in providing the necessary transparency and rigidity of said container member include polyvinyl chloride, acrylic polymers, polycarbonates, cellulose butyrate, ionomer resins and olefin terpolymers. The outside diameter of sidewall 20 is between 1.75 and 2.0 inches.

Plunger member 12 is of cylindrical rod or tube construction, elongated between forward and rearward extremities 29 and 30, respectively, said extremities having first and second transverse surfaces, 31 and 32, respectively. Said plunger member is dimensioned and configured to make close fitting insertive sliding engagement with interior surface 18 of bore 13. First transverse surface 31 is adapted to apply an advancing force to medication disposed within bore 13. A surrounding lip 33 is disposed about the circular perimeter of said first transverse surface, preferably as a continuous integral extension thereof. Said lip protrudes outwardly from the exterior side wall surface 34 of said plunger, the extent of said outward protrusion being less than 1 millimeter.

The function of lip 33 is to engage grooves 17 within the interior surface 18 of bore 13. The nature of such engagement is slight, but sufficient to produce a tactile feeling of a discontinuity in the otherwise smooth forward motion of plunger member 12 within bore 13. In some embodiments, the nature of such engagement may be such as to produce an audible click. It is further to be noted that the seated position of lip 33 within one of the grooves 17 is visually discernible because of the transparent nature of said container member.

Abutment means in the form of collar 35 extends outwardly from rearward extremity 30 of plunger member 12 as a continuous integral extension thereof. One function of collar 35 is to limit forward movement of said plunger member by way of abutment with the trailing extremity 16 of said container member. Another function of collar 35 is to permit manipulative gripping of said plunger member by the user.

In operation, the user will enter medications 21 having paste-like consistency into said container member in desired amounts employing said demarcation grooves as volumetric measuring indicia. Suitable medications are generally sold in squeeze dispensers which facilitate transfer of the medication into said container member. Plunger member 12 is then placed within bore 13 and advanced so as to obtain an accurate, squared off displacement of the medication relative to said grooves. The leading extremity 15 of said container member is then inserted into the vagina and the plunger member is depressed until a click is felt or heard or until the plunger member has come to rest by the action of abutment collar 35.

The two monolithic plastic components of the dispenser device are of such simple construction and attendant low manufacturing cost as to justify one-time use and disposal of the dispenser.

While particular examples of the present invention have been shown and described, it is apparent that changes and modifications may be made therein without departing from the invention in its broadest aspects. The aim of the appended claims, therefore is to cover all such changes and modifications as fall within the true spirit and scope of the invention.

Having thus described my invention, what is claimed is:

1. A hand-operated disposable device for controllably dispensing substances having a paste-like or cream-like consistency comprising:

a) a transparent plastic container member having a smooth exterior surface and a cylindrical bore elongated upon a straight axis between open leading and trailing extremities and having a smooth interior surface and demarcation means in the form of annular grooves fashioned within said interior surface and disposed at spaced intervals along said axis to denote successive regions within said bore of known volume, and b) a plunger member elongated between forward and rearward extremities and removably associated with said container member by way of slidable engagement with said bore upon a common axis, said forward extremity having a transverse force-applying surface and a surrounding outwardly protruding wiping lip, and said rearward extremity having abutment means to limit forward movement of said plunger member by way of abutment with the trailing extremity of said container member.

2. The device of claim 1 wherein said wiping lip is configured to seat within said grooves sufficiently to produce a tactile feeling of a discontinuity in the otherwise smooth motion of said plunger member within said bore.

3. The device of claim 2 wherein the leading extremity of said container member is rounded.

4. The device of claim 3 wherein said container member and plunger member are both of monolithic construction.

5. The device of claim 4 wherein indicia is located on the exterior surface of said container member adjacent said demarcation means to show the corresponding volume within said bore.

* * * * *